US009050331B2

(12) United States Patent
Asahara et al.

(10) Patent No.: US 9,050,331 B2
(45) Date of Patent: Jun. 9, 2015

(54) PHARMACEUTICAL FORMULATIONS COMPRISING PARAOXONASE

(75) Inventors: Naomi Asahara, Tokyo (JP); Motonori Hashimoto, Tokyo (JP); Satoshi Yuki, Tokyo (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 2200 days.

(21) Appl. No.: 10/588,513

(22) PCT Filed: Feb. 4, 2005

(86) PCT No.: PCT/JP2005/001665
§ 371 (c)(1),
(2), (4) Date: May 29, 2007

(87) PCT Pub. No.: WO2005/074977
PCT Pub. Date: Aug. 18, 2005

(65) Prior Publication Data
US 2007/0280916 A1    Dec. 6, 2007

(30) Foreign Application Priority Data
Feb. 4, 2004  (JP) .................. 2004-027727

(51) Int. Cl.
  *C12N 9/14*   (2006.01)
  *C12N 9/16*   (2006.01)
  *A61K 38/46*  (2006.01)
  *A61K 47/18*  (2006.01)

(52) U.S. Cl.
  CPC ............. *A61K 38/465* (2013.01); *A61K 47/186* (2013.01); *C12Y 301/08001* (2013.01)

(58) Field of Classification Search
  CPC ..... C12N 9/14; C12N 9/16; C12Y 301/08001
  USPC ........................................................ 424/94
  See application file for complete search history.

(56) References Cited

U.S. PATENT DOCUMENTS

| 6,391,298 | B1 | 5/2002 | Radtke |
| 6,521,226 | B1 | 2/2003 | Radtke |
| 2003/0027759 | A1 | 2/2003 | Radtke |
| 2004/0038891 | A1* | 2/2004 | Bisgaier et al. ............. 514/12 |
| 2006/0257866 | A1* | 11/2006 | Welch et al. ............... 435/6 |

FOREIGN PATENT DOCUMENTS

| EP | 0 277 096 A2 | 8/1988 |
| JP | 63 192723 | 8/1988 |
| JP | 64-47435 | 2/1989 |
| JP | 2000 109435 | 4/2000 |
| JP | 2000-333674 | 12/2000 |
| JP | 2001-204461 | 7/2001 |
| JP | 2001 515460 | 9/2001 |
| JP | 2003 526610 | 9/2003 |
| JP | 2003 342294 | 12/2003 |
| WO | WO 00/30425 | 6/2000 |
| WO | 03 097696 | 11/2003 |

OTHER PUBLICATIONS

Michael Aviram, et al., "Paraoxonase Inhibits High-density Lipoprotein Oxidation and Preserves its Functions", J. Clin. Invest., vol. 101, No. 8, Apr. 1998, pp. 1581-1590.
Diana M. Shih, et al., "Mice lacking serum paraoxonase are susceptible to organophosphate toxicity and atherosclerosis", Letters to Nature, vol. 394, Jul. 16, 1998, pp. 284-286.
RC Sorenson, et al., "Reconsideration of the Catalytic Center and Mechanism of Mammalian Paraoxonase/Arylesterase", Proceedings of the National Academy of Sciences of the United States of America, vol. 92, Aug. 1995, pp. 7187-7191.
Robert J. Brushia, et al., "Baculovirus-mediated expression and purification of human serum paraoxonase 1A", Journal of Lipid Research, vol. 42, 2001, pp. 951-958.
H. Nagasawa, et al., "Correlation between cerebral blood flow and histologic changes in a new rat model of middle cerebral artery occlusion", Stroke, vol. 20, No. 8, Aug. 1989, pp. 1037-1043 with cover page.
Yi Li, et al., "Intrastriatal Transplantation of Bone Marrow Nonhematopoietic Cells Improves Functional Recovery After Stroke in Adult Mice", Journal of Cerebral Blood Flow and Metabolism, vol. 20, No. 9, 2000, pp. 1311-1319.
Office Action issued Oct. 7, 2010, in Japan Patent Application No. 2005-517739.
Extended European Search Report issued Oct. 13, 2010, in Application No. 10168909.9-2401.
Database NTIS [Online], National Technical Information Service, US Deparment of Commerce, P Schmid, et al., "Organophosphate Detoxification", XP-002601703, Jan. 1, 1990, 1 page.
D. Josse, et al., "Paraoxonase Oligomeric Forms", (Formes Oligomériques de la Paraoxonase, vol. 0, No. 20, XP009118359, 1999, pp. 99-100.
C. Jinhua, et al., "The relationship between paraoxonase gene 192 polymorphism and atherosclerotic cerebral Infarction". International Society for Neurochemitry, Journal of Neurochemistry, vol. 87, No. Supplement 1, XP002601704, Dec. 2003, p. 147.
Karen N. Gan, et al., "Purification of Human Serum Paraoxonase/ Arylesterase Evidence for One Esterase Catalyzing Both Activities", Drug Metabolism and Disposition, vol. 19, No. 1, pp. 100-106, 1991.
Clement E. Furlong, et al., "Purification of Rabbit and Human Serum Paraoxonase", Biochemistry, vol. 30, No. 42, pp. 10133-10140, 1991.
Denis Josse, et al., "Oligomeric States of the Detergent-Solubilized Human Serum Paraoxonase (PON 1)", The Journal of Biological Chemistry, vol. 277, No. 36, pp. 33386-33397, 2002.
Takahiro Ueno, et al., "Paraoxonase 1 Polymorphism LEU-MET55 Is Associated With Cerebral Infarction in Japanese Population", Med. Sci.Monit., vol. 9, No. 6, pp. CR260-CR264, 2003.
Aihua Wu, et al., "High-Density Lipoproteins in Sepsis and Septic Shock: Metabolism, Actions, and Therapeutic Applications", Shock, vol. 21, No. 3, pp. 210-221, 2004.

* cited by examiner

*Primary Examiner* — Ruth Davis
(74) *Attorney, Agent, or Firm* — Oblon, McClelland, Maier & Neustadt, L.L.P.

(57) ABSTRACT

The present invention provides a pharmaceutical formulation comprising paraoxonase (PON), a purification and stabilization method of PON, and an agent for prophylactic and/or therapeutic treatment of a disease resulting from ischemia reperfusion and/or cerebral infarction containing PON as an active ingredient.

18 Claims, 2 Drawing Sheets

PHARMACEUTICAL FORMULATIONS COMPRISING PARAOXONASE

TECHNICAL FIELD

The present invention relates to paraoxonase (hereinafter also referred to as PON). More precisely, the present invention relates to a pharmaceutical formulations comprising PON, methods for purification and stabilization thereof, and novel medicinal uses thereof.

BACKGROUND ART

Paraoxonase (also referred to as human serum paraoxonase or PON1) is a $Ca^{2+}$-dependent glycoprotein having a molecular weight of about 45 kDa which exists as one of protein components that constitute high density lipoprotein (HDL) in blood. PON is known as a serum enzyme that degrades oxon, organophosphorous compounds, and aromatic carboxylic acids such as sarin which is a nerve gas, and can be used as an antidote for these substances. In recent years, physiological activities of PON are being elucidated. For example, antiarteriosclerotic action, antioxidative action and the like have been reported (Non-patent documents 1 and 2, Patent document 1).

As for purification of PON, methods of employing a blue agarose treatment and a DEAE-type anion exchanger treatment in combination were reported (Non-patent documents 3 and 4). According to these reports, PON was purified under the coexistence of glycerol and a polyoxyethylene alkyl phenyl ether-type non-ionic surfactants (specifically, Emulgen and Nonidet P-40, both are trade names). However, the documents do not disclose use of other substances such as, for example, 3-[(3-cholamidopropyl)dimethylammonio]-1-propane sulfonate (henceforth also referred to as CHAPS). Further, CHAPS was reported to be added in a serum specimen containing PON to maintain the enzymatic activity (Patent document 2). However, this report is not related to purified PON.

Some reports were made which suggest medicinal applications of PON. For example, a report was made which suggests relationships between an amount of PON in vivo and angina pectoris, myocardial infarction, and cerebral infarction (Patent document 2). Patent document 3 is a report relating to a disorder resulting from ischemia reperfusion in connection with Apo-A1. In the report, PON is suggested to be effective for the disorder resulting from ischemia reperfusion like Apo-A1, however, the effect thereof was not specifically disclosed.

As described above, PON is at present merely suggested to have some medicinal usefulness. Almost no report has been made as to means for stably supplying PON for medical uses.
Patent document 1: International Patent Publication WO00/30425
Patent document 2: Japanese Patent Unexamined Publication (KOKAI) No. 2000-333674
Patent document 3: International Patent Publication WO03/97696
Non-patent document 1: J. Clin. Invest., Vol. 101, pp. 1581-1590, 1998
Non-patent document 2: Nature, Vol. 394, pp. 284-287, 1998
Non-patent document 3: Drug Metabolism and Disposition, Vol. 19, No. 1, pp. 100-106,
Non-patent document 4: Biochemistry, Vol. 30, pp. 10133-10140, 1991
Non-patent document 5: Proc. Natl. Acad. Sci. USA, Vol. 92, pp. 7187-7191, 1995
Non-patent document 6: J. Lipid Research, Vol. 42, pp. 951-958, 2001
Non-patent document 7: Stroke, Vol. 20, pp. 1037-1043, 1989
Non-patent document 8: Journal of Cerebral Blood Flow and Metabolism, Vol. 20, pp. 1311-1319, 2000

DISCLOSURE OF THE INVENTION

Object to be Achieved by the Invention

It was expected to be difficult to efficiently recover a highly purified PON by the conventional methods. Further, conventionally-used surfactants, e.g., polyoxyethylene alkyl phenyl ether-type non-ionic surfactants, were not satisfactory in stabilizing PON activities. Further, among these surfactants, those having a high molecular weight cannot be removed by dialysis or the like. Accordingly, if PON purified by chromatography is concentrated for administration to animals and the like, the surfactants are also concentrated together, and their adverse effects on living bodies are concerned.

An object of the present invention is to provide a technical means for purifying and formulating PON so as to be clinically applicable. Another object of the present invention is to provide a novel medicinal uses of PON.

Means for Achieving the Object

The inventors of the present invention conducted various researches in consideration of the circumstances as described above. As a result, they found that purity, expression, recovery and stability of PON activities were successfully improved by addition of CHAPS at the time of purification and/or storage of PON.

Further, the inventors of the present invention verified that PON was effective in an ischemia reperfusion animal model.

The present inventions are follows:
(1) A pharmaceutical formulation comprising PON, which contains PON and CHAPS.
(2) The pharmaceutical formulation according to (1), which further contains a polyol.
(3) The pharmaceutical formulation according to (2), wherein the polyol is glycerol.
(4) A method for purifying PON, which comprises subjecting a solution containing PON to a hydrophobic carrier treatment and then to an anion exchanger treatment in the presence of CHAPS.
(5) The purification method according to (4), wherein the anion exchanger treatment is performed in the presence of CHAPS and a polyol.
(6) The purification method according to (5), wherein the polyol is glycerol.
(7) A method for stabilizing PON, which comprises adding CHAPS to PON.
(8) The stabilization method according to (7), which further comprises adding a polyol.
(9) The stabilization method according to (8), wherein the polyol is glycerol.
(10) An agent for prophylactic and/or therapeutic treatment of a disorder resulting from ischemia reperfusion and/or cerebral infarction, which comprises PON as an active ingredient.
(11) The agent for prophylactic and/or therapeutic treatment according to (10), which is used for improving prognosis, neurological symptoms, or motor dysfunction of a disease resulting from ischemia reperfusion and/or cerebral infarction.

(12) An agent for prophylactic and/or therapeutic treatment of a disease resulting from ischemia reperfusion and/or cerebral infarction, which comprises PON and CHAPS.
(13) The agent according to (12), which is used for improving prognosis, neurological symptoms, or motor dysfunction of a disease resulting from ischemia reperfusion and/or cerebral infarction.
(14) The agent according to (12) or (13), which further contains a polyol.
(15) The agent according to (14), wherein the polyol is glycerol.
(16) A method for improving prognosis, neurological symptoms, or motor dysfunction of a disease resulting from ischemia reperfusion and/or cerebral infarction, which comprises administering an effective amount of PON.
(17) Use of PON for the manufacture of the agent for improving prognosis, neurological symptoms, or motor dysfunction of a disease resulting from ischemia reperfusion and/or cerebral infarction.

Effect of the Invention

According to the present invention, pharmaceutical formulation comprising PON can be provided which has improved stability at the time of purification and storage. Further, a novel medicament useful for treatment of a disease resulting from ischemia reperfusion and/or cerebral infarction can be provided.

BEST MODE FOR CARRYING OUT THE INVENTION

Starting Material

Figure 1:
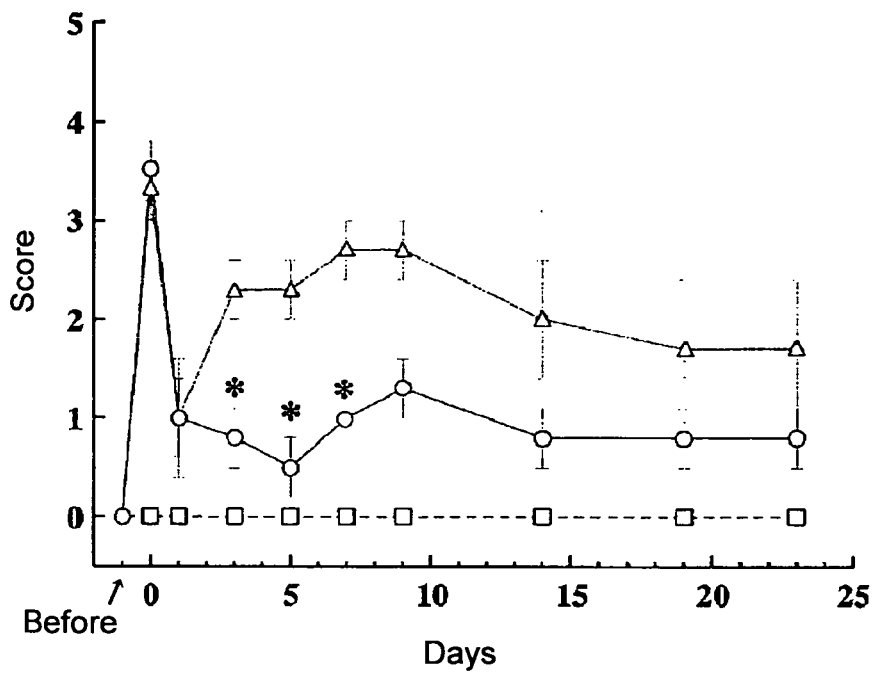
FIG. 1 shows changes with time in improvements of neurological symptoms of ischemia reperfusion model animal, when PON was initially administered immediately after reperfusion. The horizontal axis represents observation days, that is, the days after the reperfusion (day), and the vertical axis represents neurological symptom scores. The symbols, □, Δ, and ○, used in the graph represent neurological symptom scores on each observation day. Each data is represented as mean±SEM. Among combinations of symbols and polygonal lines, the combination of □ and a dotted line represents the results of a sham group (normal group), the combination of Δ and a dotted line represents the results of a vehicle group (disease group), and the combination of ○ and a solid line represents a PON-administered group. The symbol * means the presence of a significant difference with a critical rate less than 5% in comparison with the vehicle group determined by the Wilcoxon test.

The starting material used for the present invention is not particularly limited so long as the material is a solution containing PON. Examples thereof include blood, plasma, serum, plasma from which fibrin is removed, a supernatant fraction obtained from plasma by the cold ethanol fractionation technique of Cohn, Eff.I, and the like. Further, the solution containing PON may be prepared by utilizing recombinant DNA technologies. Specifically, a solution containing recombinant PON expressed in CHO cells, insect cells or the like by recombinant DNA technologies (e.g., culture broth, culture supernatant and the like) can be used (see, Non-patent documents 5 and 6).

Purification

The purification method of the present invention is characterized by subjecting the solution containing PON to a hydrophobic carrier treatment and then to an anion exchanger treatment in the presence of a polyol and CHAPS. Alternatively, the purification method of the present invention is characterized by subjecting a solution containing PON to a hydrophobic carrier treatment and then to an anion exchanger treatment in the presence of CHAPS.

Hydrophobic Carrier Treatment

The hydrophobic carrier is an insoluble carrier bound with a hydrophobic group. Examples of the insoluble carrier include agarose (Sepharose (trade name) and the like), crosslinked dextran (Sephadex (trade name) and the like), hydrophilic vinyl polymers (TOYOPEARL (trade name) and the like) and the like. Further, examples of the hydrophobic group include an alkyl group, preferably an alkyl group having 4 to 18 carbon atoms (e.g., butyl group, octyl group, octadecyl group and the like), phenyl group and the like. The hydrophobic group can be bound to the insoluble carrier by a known method. The hydrophobic carrier can also be obtained as a commercially available product.

As methods of hydrophobic carrier treatment, specifically, a solution containing PON is brought into contact with a hydrophobic carrier so that PON should be adsorbed to the hydrophobic carrier, and then PON is recovered by eluting it with an appropriate solution. The adsorption conditions include pH of about 6 to 8 and a salt concentration of about 0.01 to 0.2 M. Further, about 0.1 to 2 mM of a calcium salt may be added. Specifically, a physiological saline (0.15 M sodium chloride) containing 1 mM calcium chloride and the like can be exemplified. When washing is performed after the adsorption, it can be performed under the same conditions as the adsorption.

An alkylene glycol having 1 to 4 carbon atoms (e.g., ethylene glycol and the like) of 30 to 70 w/v %, preferably about 40 to 60 w/v %, is used for the elution. Further, 0.1 to 2 mM of a calcium salt may be added. Specifically, an aqueous solution containing 50 w/v % ethylene glycol and 1 mM calcium chloride and the like can be exemplified.

Anion Exchanger Treatment

The anion exchanger is an insoluble carrier bound with an anion exchange group. Examples of the insoluble carrier include agarose (Sepharose (trade name) and the like), crosslinked dextran (Sephadex (trade name) and the like), hydrophilic vinyl polymers (TOYOPEARL (trade name) and the like) and the like. Further, examples of the anion exchange group include diethylaminoethyl group (DEAE type), quaternary ammonium group (Q type), quaternary aminoethyl group (QAE type) and the like. Preferably, a strongly basic group such as a quaternary ammonium group and quaternary aminoethyl group is used. The anion exchange group can be bound to the insoluble carrier by a known method. The anion exchanger can also be obtained as a commercially available product.

The anion exchanger treatment is performed under the coexistence of a polyol (e.g., glycerol and the like) and CHAPS(N,N-dimethyl-N-(3-sulfopropyl)-3-[[(3α,5β,7α,12α)-3,7,12-trihydroxy-24-oxocholan-24-yl]-amino]-1-propanamium or 3-[(3-cholamidopropyl)dimethylammonio]-1-propanesulfonate). The amount of the polyol to be added is, for example, about 10 to 40 w/v %, preferably about 20 to 30 w/v %. The amount of CHAPS to be added is, for example, about 0.01 to 1 w/v %. When further purification is performed after the above treatment, any purification should be performed under the coexistence of a polyol and CHAPS.

The anion exchanger treatment can also be performed in the presence of CHAPS. When further purification is performed after the above treatment, any treatment may be performed in the presence of CHAPS.

As methods of the anion exchanger treatment, specifically, a solution containing PON is contacted with an anion exchanger so that PON is adsorbed to the anion exchanger, and then PON is recovered by elution with a solvent having a high salt concentration. The adsorption conditions include a pH of about 6 to 9 and a salt concentration of about 0.001 to 0.1 M. Further, about 0.1 to 2 mM of a calcium salt may be added. Specifically, a 25 mM Tris-hydrochloride buffer (pH 7.5) containing 1 mM calcium chloride, 25 w/v % glycerol, and 0.5 w/v % CHAPS and the like can be exemplified. When washing is performed after the adsorption, the process can be performed under the same conditions as those in the adsorption. The elution conditions include a pH of 6 to 9 and a salt concentration of about 0.1 to 2 M. Further, about 0.1 to 2 mM of a calcium salt may be added. Specifically, a 25 mM Tris-hydrochloride buffer (pH 7.5) containing 0.1 to 1 M sodium chloride, 1 mM calcium chloride, 25 w/v % glycerol, and 0.5 w/v % CHAPS and the like can be exemplified. The elution may be performed by either methods of stepwise increase of a salt concentration or methods of continuous increase thereof (concentration gradient method).

Concentration (Ultrafiltration)

After the anion exchanger treatment, the solution containing PON can be concentrated by using an ultrafiltration membrane having a cut-off molecular weight of about 10 to 30 kDa.

Immobilized Concanavalin A (Hereinafter Also Referred to as ConA) Treatment

Immobilized ConA is an insoluble carrier bound with ConA. Examples of the insoluble carrier include agarose (Sepharose (trade name) and the like), crosslinked dextran (Sephadex (trade name) and the like), hydrophilic vinyl polymers (TOYOPEARL (trade name) and the like) and the like. ConA can be bound to the insoluble carrier by a known method. The immobilized ConA can also be obtained as a commercially available product.

As methods for the immobilized ConA treatment, specifically, a solution containing PON is contacted with immobilized ConA so that PON is adsorbed to the immobilized ConA, and then PON is recovered by elution with a solvent having a high salt concentration or an appropriate solution. The adsorption conditions include a pH of about 6 to 9 and a salt concentration of about 0.1 to 0.5 M. Further, about 1 to 20 mM of a calcium salt and about 1 to 10 μM of an EDTA salt (e.g., alkaline earth metal salts such as sodium salts and potassium salts) may be added. Specifically, a 25 mM Tris-hydrochloride buffer (pH 7.5) containing 10 mM calcium chloride, 0.2 M sodium chloride, 5 μM EDTA trisodium salt, 25 w/v % glycerol and 0.5 w/v % CHAPS and the like can be exemplified. When washing is performed after the adsorption, the process can be performed under the same conditions as those for the adsorption.

The elution conditions include pH of 6 to 9 and a salt concentration of about 1 to 5 M. Alternatively, about 0.1 to 0.5 M α-methyl mannoside is used under the same pH and salt concentration as those for the adsorption conditions. Further, about 1 to 20 mM of a calcium salt and about 1 to 10 μM of an EDTA salt (e.g., alkaline earth metal salts such as sodium salts and potassium salts and the like) may be added. Specifically, a 25 mM Tris-hydrochloride buffer (pH 7.5) containing 10 mM calcium chloride, 1 to 4 M sodium chloride, 5 μM EDTA trisodium salt, 25 w/v % glycerol and 0.5 w/v % CHAPS, a 25 mM Tris-hydrochloric acid buffer (pH 7.5) containing 0.1 to 0.5 M α-methyl mannoside, 10 mM calcium chloride, 0.2 M sodium chloride, 5 μM EDTA trisodium salt, 25 w/v % glycerol and 0.5 w/v % CHAPS and the like can be exemplified. The elution can be performed by either methods of stepwise increase of the salt concentration or the α-methyl mannoside concentration or methods of continuous increase thereof (concentration gradient method). The immobilized ConA treatment may be performed as required, and the treatment can be omitted if desired.

Anion Exchanger Treatment (Second Time)

This anion exchanger treatment can be performed by repeating the first anion exchanger treatment in the same manner.

In order to further improve purity of PON, a blue agarose treatment can be performed in combination as a known technique. As for the conditions of the treatment, the treatment can be performed according to a known method. As described above, however, the treatment is performed under the coexistence of a polyol and CHAPS. Alternatively, this treatment can be performed in the presence of CHAPS.

Specific examples of the purification method of the present invention include methods comprising the following treatments.

Hydrophobic carrier treatment→anion exchanger treatment→immobilized ConA treatment→anion exchanger treatment (second time)

Hydrophobic carrier treatment→anion exchanger treatment→anion exchanger treatment (second time)

According to the purification method, PON highly purified to 100 to 2000 U/$A_{280}$, preferably about 500 to 1800 U/$A_{280}$, can be prepared. One unit (1 U) of PON activity means that 1 nmol of paraoxon is hydrolyzed to 4-aminophenol of the same molar amount per minute. Details are as described in Reference Example 1.

Pharmaceutical Formulation

A pharmaceutical formulation is prepared by using the purified PON. As the purified PON, those prepared by the aforementioned purification method can be used. Further, those prepared by known purification methods can also be used. Examples the methods include those comprising a blue agarose treatment and an anion exchanger treatment in combination (Patent document 2, Non-patent documents 3 and 4) and the like.

An example of a concentration of PON in the pharmaceutical formulation includes, for example, about 1 to 100 mg/mL (1800 to 180,000 U/mL). An example of a pH includes, for example, about 6 to 9, and an example of a salt concentration includes, for example, about 1 to 100 mM. Examples of additives include a polyol, CHAPS and the like. Examples of the polyol include glycerol and the like. An example of a concentration of the polyol to be added includes, for example, about 1 to 5 w/v %, and an example of that of CHAPS includes, for example, about 0.001 to 0.1 w/v %. Further, a calcium salt such as calcium chloride, a chelating agent such as EDTA, and a buffer such as Tris may be used. An example of a concentration of the calcium salt to be added includes, for example, about 0.01 to 1 mM, an example of that of the chelating agent includes, for example, about 0.1 to 1 µM, and an example of that of the buffer includes, for example, about 1 to 10 mM.

If necessary, various additives can be added to the solution containing PON, and pharmaceutical formulations containing PON can be prepared by sterilization with filtration, packaging into small sizes, lyophilization and the like.

Administration and Dosage

The pharmaceutical preparation comprising PON obtained according to the present invention can be used for known medicinal uses. Examples thereof include use as an antidote and application to arteriosclerosis. Further, as novel pharmaceutical uses, the preparation can be applied to prophylactic and/or therapeutic treatment of a disease resulting from ischemia reperfusion and/or cerebral infarction and the like. A routs of administration may be either oral administration or parenteral administration. Examples of the parenteral administration include injections such as intravenous injection and the like. The dose can be appropriately increased or decreased depending on symptoms, sexuality, age and body weight of a patient and the like. Specifically, an example of the dose includes, for example, about 0.1 to 1000 mg/kg of body weight.

In particular, where PON is used for prophylactic and/or therapeutic treatment of a disease resulting from ischemia reperfusion and/or cerebral infarction, the preparation can be used for, specifically, improvement of prognosis, neurological symptoms, or motor dysfunction of a disease resulting from ischemia reperfusion and/or cerebral infarction. Further, PON can be used for prophylactic and/or therapeutic treatment of consciousness disorder in a disease resulting from ischemia reperfusion and/or cerebral infarction, as well as neurological symptoms, motor disability, in particular, activities of daily living disability, functional disorder and the like with these diseases.

Specific examples of administration methods for using PON for prophylactic and/or therapeutic treatment of a disease resulting from ischemia reperfusion and/or cerebral infarction include an administration once a day, i.e. once or daily for 1 to 14 days, preferably 1 to 7 days, wherein the administration is started within 48 hours, preferably within 24 hours, more preferably within 12 hours, most preferably within 3 hours, after the onset of a disease resulting from ischemia reperfusion and/or cerebral infarction.

EXAMPLES

For more detailed explanation of the present invention, the following examples and test examples will be described. However, the scope of the present invention is not limited by these examples.

Reference Example 1

A. Measurement of PON Activity

1) Preparation of Substrate

In a volume of 7 µL of a substrate stock solution (paraoxon, also referred to as diethyl p-nitro-phenyl phosphate, Sigma) was dissolved in 52 µL of DMSO and then diluted 100 times with 0.1 M Tris-hydrochloride buffer, 2 mM calcium chloride (pH 8, 25° C.). The aforementioned buffer added with heparin (0.5 mg/mL) was used for this measurement system as required.

2) Measurement (Performed at Room Temperature)

In a volume of 20 µL of a sample (containing PON) and 200 µL of the substrate solution prepared in 1) were added to a 96-well microplate and mixed (the final concentration of paraoxon was 5 mM). Absorbance at a wavelength of 405 nm was measured in a kinetic mode for 30 minutes, and the results were calculated by using Softmax Version 2.35. The sample was diluted with the same buffer as that used for the preparation of the substrate.

3) Method for Calculating Activity

Activity was calculated by using the $V_{max}$ in mOD/min obtained in 2) in accordance with the following equation. The values with a $V_{max}$ correlation coefficient of 0.95 or higher were used.

$$\text{PON activity (U/mL=nmol/min/mL)} = V_{max} \text{ in mOD/min}/17000/0.6 \times 0.22 \times 1000 \times 50 \qquad \text{Equation 1}$$

B. The PON Antigen Level was Measured by the Sandwich ELISA Method

Example 1

PON was purified by using serum prepared from pooled human plasma. The human serum was applied to a phenyl-agarose column (Phenyl Sepharose, Amersham Pharmacia) equilibrated with physiological saline containing 1 mM calcium chloride. The column was washed with the same solvent, and then the adsorbed PON was eluted with an aqueous solution containing 50 w/v % ethylene glycol and 1 mM calcium chloride. This solution was desalted and concentrated by using an ultrafiltration membrane (30 kDa) with a 25 mM Tris-hydrochloride buffer (pH 7.5) containing 1 mM calcium chloride, 25 w/v % glycerol and 0.5 w/v % CHAPS, and applied to a quaternary ammonium type-agarose column (Q-Sepharose, Pharmacia) equilibrated with the same solution. After the column was washed with the same solution, elution was performed with a sodium chloride concentration increasing stepwise in the order of 0.1 M→0.15 M→0.2 M→0.25 M→1 M. The fractions eluted with 0.2 M to 0.25 M sodium chloride were collected and concentrated by using an ultrafiltration membrane (10 kDa).

Example 2

The solution containing PON prepared in Example 1 was applied to a ConA agarose column (ConA Sepharose, Amersham Pharmacia) equilibrated with a 25 mM Tris-hydrochloride buffer (pH 7.5) containing 10 mM calcium chloride, 0.2 M sodium chloride, 5 µM EDTA trisodium salt, 25 w/v % glycerol and 0.5 w/v % CHAPS. The column was washed with the same solution, and then PON was eluted with the same solution containing 3 M sodium chloride. The solution was concentrated by using an ultrafiltration membrane (10 kDa). This solution was applied to a quaternary ammonium type agarose column (mentioned above) in the same manner as in Example 1, and the fraction eluted with 0.25 M sodium chloride was collected. The activity recovery ratio was 95% after the aforementioned quaternary ammonium-type agarose treatment (second time). Further, when the purified PON was analyzed by SDS-PAGE (under a reduced condition), PON was detected as a substantially single band (molecular weight: 45 kDa).

Example 3

The experiment was performed in the same manner as in Example 1 except that the sodium chloride concentration at the time of elution in the quaternary ammonium-type agarose (Q-Sepharose) treatment was increased stepwise in the order of 0.15 M→0.2 M→0.25 M→1 M. The fraction eluted with 0.25 M sodium chloride was collected and concentrated by using an ultrafiltration membrane (10 kDa).

Example 4

The solution containing PON prepared in Example 3 was applied again to the quaternary ammonium-type agarose column in the same manner as in Example 1, and a fraction eluted with 0.2 M sodium chloride was collected. When the purified PON was analyzed by SDS-PAGE (under a reducing condition), PON was detected as a substantially single band (molecular weight: 45 kDa).

The purification behavior of PON at each purification step is shown in the following tables. Example 1 corresponds to Tables 1 and 2, Example 2 corresponds to Table 3, Example 3 corresponds to Table 4, and Example 4 corresponds to Table 5.

TABLE 1

Table 1

| Specimen | Volume (mL) | $A_{280}$ recovery ratio (%) | Recovered activity ratio (%) | Specific activity (U/$A_{280}$) |
|---|---|---|---|---|
| Serum | 144 | 100 | 100 | 2.14 |
| After hydrophobic carrier treatment | 250 | 4.2 | 66.4 | 31.93 |

TABLE 2

Table 2

| Specimen | Volume (mL) | $A_{280}$ recovery ratio (%) | Recovered activity ratio (%) | Specific activity (U/$A_{280}$) |
|---|---|---|---|---|
| Solution treated with hydrophobic carrier | 10 | 100 | 100 | 32.91 |
| After anion exchanger treatment (fraction eluted with 0.2 M sodium chloride) | 25 | 16.8 | 65.2 | 126.88 |
| Same as above (fraction eluted with 0.25 M sodium chloride) | 25 | 5.9 | 26.1 | 139.06 |

TABLE 3

Table 3

| Specimen | Volume (mL) | $A_{280}$ recovery ratio (%) | Recovered activity ratio (%) | Specific activity (U/$A_{280}$) |
|---|---|---|---|---|
| Solution treated with anion exchanger | 4 | 100 | 100 | 182.7 |
| After immobilized ConA treatment | 4.9 | 7.4 | 31.4 | 777.4 |

TABLE 4

Table 4

| Specimen | Volume (mL) | $A_{280}$ recovery ratio (%) | Recovered activity ratio (%) | Specific activity (U/$A_{280}$) |
|---|---|---|---|---|
| Solution treated with hydrophobic carrier | 286 | 100 | 100 | 32.41 |
| After anion exchanger treatment | 250 | 8.6 | 62.9 | 266.04 |

TABLE 5

Table 5

| Specimen | Volume (mL) | $A_{280}$ recovery ratio (%) | Recovered activity ratio (%) | Specific activity (U/$A_{280}$) |
|---|---|---|---|---|
| Solution treated with anion exchanger | 12 | 100 | 100 | 266.04 |
| After 2nd anion exchanger treatment | 25 | 14.0 | 57.0 | 1800.00 |

Example 5

A PON preparation having a composition of 10 mg/mL purified PON (prepared in Example 4) and a 2.5 mM tris-hydrochloride (pH 7.5) containing 2.5 w/v % glycerol, 0.05 w/v % CHAPS, 0.1 mM calcium chloride, 20 mM sodium chloride and 0.5 µM EDTA.3Na was prepared.

Experimental Example 1

The eluate obtained after the treatment with a hydrophobic carrier (phenyl agarose, also used in the following Experimental Examples and Reference Example 2) in Example 1 was used to test the effects of various detergents (polyoxyethylene alkyl phenyl ether (trade name: Triton X-100), polyoxyethylene sorbitan fatty acid ester (trade name: Tween 80), octylthioglucoside, CHAPS) and the activity remaining ratio. A 25 mM Tris-hydrochloride buffer (pH 7.5) containing 1 mM calcium chloride and 25 w/v % glycerol was used. The mixtures were left stand at room temperature for 30 minutes, and then PON activity was measured. The results are shown in Table 6.

TABLE 6

Table 6

| Type of detergent | Concentration of added surfactant (%) | Activity remaining ratio (%) |
|---|---|---|
| Immediately before | | 100 |
| Triton X-100 | 0.1 | 70 |
| Tween 80 | 0.1 | 65 |
| Octylthioglucoside | 0.25 | 80 |
| CHAPS | 0.5 | 98 |

It was found that a higher activity remaining ratio was observed with CHAPS compared with Triton X-100, Tween 80 and octylthioglucoside, and thus CHAPS had a more superior stabilization effect.

Reference Example 2

The eluate obtained after the hydrophobic carrier treatment was applied to an anion exchange (DEAE-type agarose) column equilibrated with 25 mM Tris-hydrochloride buffer (pH 7.4) containing 1 mM calcium chloride, 25 w/v % glycerol and one of various detergents (polyoxyethylene alkylphenyl ether (trade name: Triton X-100), polyoxyethylene fatty acid ester (trade name: Tween 80), octylglucoside), and PON was eluted with 0.15 M sodium chloride. The concentrations of Triton X-100 and Tween 80 added were 0.1 w/v %, and the concentration of octylglucoside added was 0.5 w/v %. The results are shown in Table 7.

TABLE 7

Table 7

| Specimen | | $A_{280}$ recovery ratio (%) | Recovered activity ratio (%) | Specific activity ($U/A_{280}$) |
|---|---|---|---|---|
| Triton X-100 | Solution treated with hydrophobic carrier | 100 | 100 | 30.61 |
| | After anion exchanger treatment | 14.6 | 95.0 | 149.44 |
| Tween 80 | Solution treated with hydrophobic carrier | 100 | 100 | 28.83 |
| | After anion exchanger treatment | 35.6 | 54.3 | 121.74 |
| Octyl-glucoside | Solution treated with hydrophobic carrier | 100 | 100 | 36.08 |
| | After anion exchanger treatment | 30.5 | 49.6 | 58.43 |

Although the degree of purification (specific activity) observed with Tween 80 was comparable to that observed with Triton X-100, the recovered activity ratio was a half of that observed with Triton X-100. The degree of purification and the recovered activity ratio observed with octylglucoside were both slightly lower to those observed with Triton X-100 and Tween 80. When octylthioglucoside was used, the degree of purification and the recovered activity ratio were both comparable to those observed with octylglucoside (data not shown).

Experimental Example 2

The eluate obtained after the hydrophobic carrier treatment was applied to an anion exchange (quaternary ammonium-type agarose) column equilibrated with a 25 mM Tris-hydrochloride buffer (pH 7.5) containing 1 mM calcium chloride, 25 w/v % glycerol and 0.5 w/v % CHAPS, and eluted with 0.2 to 0.25 M sodium chloride to confirm the elution behavior of PON. The results are shown in Table 8.

TABLE 8

Table 8

| Surfactant | $A_{280}$ recovery ratio (%) | Recovered activity ratio (%) | Specific activity ($U/A_{280}$) |
|---|---|---|---|
| Solution treated with hydrophobic carrier | 100 | 100 | 32.91 |
| 0.5% CHAPS | 22.7 | 80 | 129 |

When CHAPS was used, the degree of purification and the recovered activity ratio were similar to those obtained with Triton X-100 in Reference Example 2. Further, even after this composition was stored at 4° C. for 1 month, the activity was maintained.

Experimental Example 3

The eluate obtained after the hydrophobic carrier treatment was applied to an anion exchange (quaternary ammonium-type agarose) column equilibrated with a 25 mM Tris-hydrochloride buffer (pH 7.5) containing 1 mM calcium chloride, 5 μM EDTA.3Na, 0.5 w/v % CHAPS and 25 w/v % glycerol, and eluted with 0.2 to 0.25 M sodium chloride to confirm elution behavior of PON. As a control, the solution not containing glycerol was used. The results are shown in Table 9.

TABLE 9

Table 9

| Additive | $A_{280}$ recovery ratio (%) | Recovered activity ratio (%) | Specific activity ($U/A_{280}$) |
|---|---|---|---|
| Solution treated with hydrophobic carrier | 100 | 100 | 32.91 |
| CHAPS + glycerol | 22.7 | 80 | 129 |
| CHAPS | 13.4 | 64 | 152 |

A lower recovered activity ratio was observed when glycerol was not added. Further, as for stability of the applied sample and the obtained fractions, about 50% of decrease in the activity was observed after storage for 1 week.

Experimental Example 4

The effect of the purified PON on a rat cerebral infarction (ischemia reperfusion) model was evaluated on the basis of the infarction lesion volume as an index.

Experimental Method

1. Test substance and preparation method thereof
   PON dissolved in a solvent at a concentration of 10 mg/mL in the same manner as in Example 5 was used. As the solvent, only the solvent used for the test substance was used.
2. Male CD (SD) rats (body weight: about 300 g, 8-week old) were used as animals.
3. Infarction lesion volume was evaluated.
4. Type of group and dose
   As a control group, the solvent was administered to the rats (n=6) from the caudal vein immediately after ischemia. As a PON-treated group, 10 mg/kg body weight was administered to the rats (n=5) from the caudal vein immediately after ischemia.

5. Method
Preparation of Ischemia Reperfusion Model

A cerebral ischemia reperfusion model was performed according to the method disclosed in Non-patent document 7. That is, animals were fixed in the dorsal position under halothane anesthesia, hair was removed from the neck, and median incision was performed in the neck skin. The common carotid artery was separated from surrounding tissues, the right external carotid artery and the common carotid artery were ligated with a silk thread. A thread was placed on the internal carotid artery, then a suture coated with silicon in a diameter of 0.45 mm (4-0 nylon thread, Kyowa Tokei Kogyo) for about 2 cm at the end was inserted 18 mm from the branching of the internal carotid artery and the external carotid artery, ligated and fixed with the silk thread together with the internal carotid artery to make the right middle cerebral artery (MCA) perfusion region ischemic. The incised part was sutured, and animals were waken from anesthesia. After ischemia for 2 hours, the incised part was opened again. Reperfusion was performed for the right MCA perfusion region by pulling out the suture for about 1 cm, and the incised part was sutured again.

Measurement of Infarction Lesion Volume

Twenty four hours after the reperfusion, each animal was decapitated, craniotomy was performed along the suture of the skull bone, and brain tissues were extracted and sectionally cut at 3 mm and 1 mm forward (+) from the bregma and 1 mm, 3 mm and 5 mm backward (−) from the bregma by using a brain slicer (RBM-4000C, Brain Matrix) to prepare coronary sections. Each brain section was subsequently incubated in 0.1 M phosphate buffer containing 2% of 2,3,5-triphenyltetrazolium chloride (TTC, Nacalai) for about 10 minutes. The brain section was taken out and photographed after moisture was lightly removed. TTC stained positive regions and negative regions were distinguished. The infarction lesion areas were measured from them by using an image analyzer (Simple PCI, C-IMAGING Systems) to calculate the infarction lesion volume.

6. The results are shown in Table 10.

TABLE 10

Table 10

| | Number of animals | Volume of cerebral infarction (mm$^2$) |
|---|---|---|
| Control group | 6 | 422.5 ± 36.4 |
| PON-treated group | 5 | 290.4 ± 42.6* |

The symbol * means that a significant difference was observed with a critical ratio less than 5%.

It was confirmed for the first time in an animal experiment that a disease resulting from ischemia reperfusion and/or cerebral infarction was significantly inhibited by administration of PON.

Experimental Example 5

1) Neurological Symptoms

Middle Cerebral Artery (MCA) Ischemia Reperfusion Model

Animals were anesthetized by inhalation with sevoflurane and fixed in the dorsal position on a heated mat (SMS-2000J, Medical System Inc., set at 37° C.). After incision of the middle of the neck, the right external carotid artery and the right common carotid artery were ligated. A suture coated with silicon in a diameter of 0.19 to 0.20 mm for about 2 cm at the end (No. 0.2 fishing line for mountain stream fishing, Owner Co., Ltd) was inserted about 0.9 cm along the right internal carotid artery from the branching of the internal carotid artery and the external carotid artery to make MCA ischemic. The incised part of the neck was sutured, and the animals were waken from anesthesia. One hour after ischemia, the animals were anesthetized in the same manner as described above, and the suture was removed to allow reperfusion of MCA. Whether the model was successfully prepared was confirmed by neurological symptoms immediately before the reperfusion, more specifically, by checking whether the left forelimb was flexed and the trunk was flexed toward the left when the animal was hung by the tail. Further, as a sham-operation group, animals in which only the right external carotid artery and the right common carotid artery were ligated and the suture was not inserted were prepared.

Neurological Symptom Score (Modified Neurologic Severity Score (NSS))

The animals were rated with scores according to the method described in Non-patent document 8. Specifically, when the following symptoms were observed, 1 point was added for each item, and the score was obtained as the total number of points.

Observation was performed 1, 3, 5, 7, 9, 14, 19 and 23 days after the reperfusion.

Symptoms counted as 1 point:
When hung by the tail, the left forelimb is flexed.
When hung by the tail, the left hindlimb is flexed.
When hung by the tail, the trunk is flexed toward the left.
When placed on the floor, the animal cannot walk straight.
When placed on the floor, the animal turns toward the left.
When placed on the floor, the animal inclines toward the left.
No movement.
A tremor.
A seizure.

Administration of Agent

PON (prepared in Example 5) was administered immediately after the reperfusion and once a day 1, 2, 3, 4, 5 and 6 days after reperfusion. The dose for each administration was 10 mg/10 mL/kg body weight. As a control, only a vehicle not containing PON was given in the same volume (vehicle group).

As for number of animals, the sham group consisted of 5 animals, the vehicle group consisted 3 animals, and the PON-treated group consisted of 4 animals. The results are shown in FIG. 1.

2) Motor Function

Figure 2:
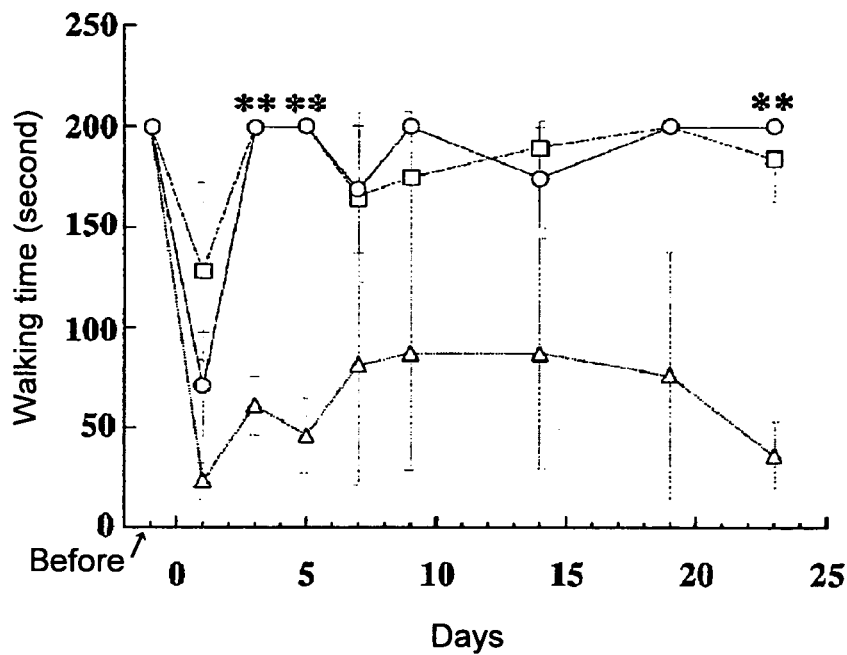
FIG. 2 shows changes with time in improvements of motor function of ischemia reperfusion model animal, when PON was initially administered immediately after reperfusion. The definitions of the horizontal axis, data indication schemes, and combinations of symbols and polygonal lines are the same as those in the explanation of FIG. 1. The vertical axis represents Rotarod walking time (second). The symbols, □, Δ, and ○, used in the graph represent the Rotarod walking times on each observation day. The symbol ** means the presence of a significant difference with a critical rate less than 1% in comparison with the vehicle group determined by the t-test.

Motor function was measured by using a commercially available Rota-rod treadmill for mice (MK-600, Muromachi Kikai Co., Ltd.). Specifically, 1, 3, 5, 7, 9, 14, 19 and 23 days after reperfusion, the animals were made to walk on a rod rotating at a constant speed (set at level 1) in the direction opposite to the rotation of the rod, and the time from the start of walking to the fall from the rod was measured. The walking time was measured up to 200 seconds. Mice practiced walking beforehand for 5 days before the test, and only animals which could walk for 200 seconds on the day before the test were used for the preparation of the middle cerebral artery (MCA) ischemia reperfusion model. Other procedures were the same as in 1). The results are shown in FIG. 2.

From these results, it was revealed that neurological symptoms and motor function were improved by administering PON to the MCA ischemia reperfusion model immediately after the reperfusion. More specifically, the prognosis improving effect of PON in the MCA ischemia reperfusion model was confirmed.

Experimental Example 6

Figure 3:
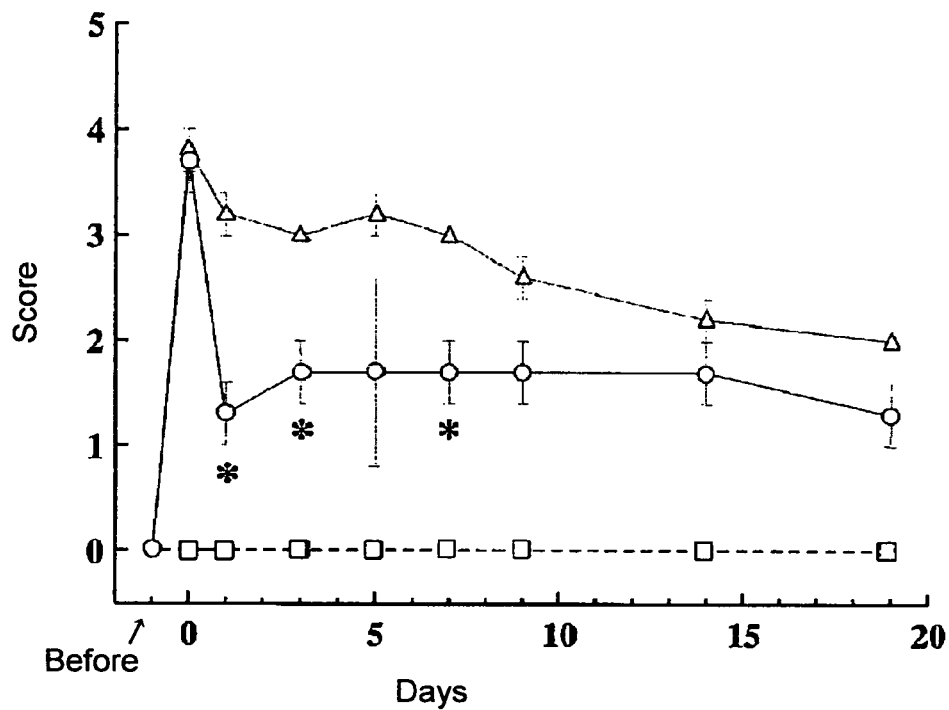
FIG. 3 shows changes with time in improvements of neurological symptoms of ischemia reperfusion model animal, when PON was initially administered after 3 hours from the reperfusion. The definitions of the horizontal axis, vertical axis, symbols, data indication schemes, and combinations of symbols and polygonal lines are the same as those in the explanation of FIG. 1. The symbol * means the presence of a significant difference with a critical rate less than 5% in comparison with the vehicle group determined by the t-test.

An experiment was performed in the same manner as in Experimental Example 5 except that PON was initially administered 3 hours after the reperfusion, and neurological symptoms were observed. As for the number of animals, the sham group consisted of 5 animals, the vehicle group consisted of 3 animals and the PON-treated group consisted of 4 animals. The results are shown in FIG. 3

Figure 4:
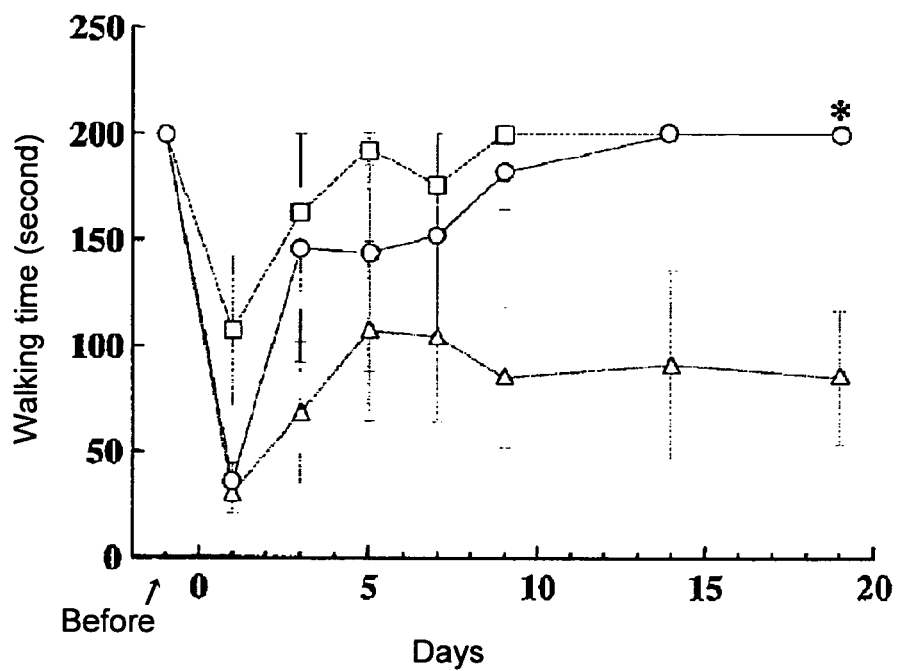
FIG. 4 shows changes with time in improvements of motor function of ischemia reperfusion model animal, when PON was initially administered after 3 hours from the reperfusion. The definitions of the horizontal axis, data indication schemes, and combinations of symbols and polygonal lines are the same as those in the explanation of FIG. 1. The definitions of the vertical axis and symbols are the same as those in the explanation of FIG. 2. The definition of symbol * is the same as that in the explanation of FIG. 3.

Further, motor function was similarly observed. As for the number of animals, the sham group consisted of 4 animals, the vehicle group consisted of 5 animals, and the PON-treated group consisted of 4 animals. The results are shown in FIG. 4.

From these results, it was revealed that neurological symptoms and motor function were also improved by administering PON to the MCA ischemia reperfusion model 3 hours after the reperfusion. More specifically, the prognosis improving effect of PON in the MCA ischemia reperfusion model was also confirmed in the animals where the initial administration of PON was 3 hours after the reperfusion.

INDUSTRIAL APPLICABILITY

According to the present invention, pharmaceutical formulations comprising PON can be provided which has improved stability at the time of purification and storage. Further, a novel medicament useful for a disease resulting from ischemia reperfusion and/or cerebral infarction can be provided.

Although the present invention has been described in detail for specific embodiments thereof, it is apparent to those skilled in the art that various alterations and modifications are conductible without departing from the spirit and scope of the present invention.

This application is based on Japanese Patent Application No. 2004-27727 (filing date: Feb. 4, 2004), of which whole disclosure is incorporated herein by reference.

What is claimed is:

1. A method for improving prognosis, neurological symptoms, or motor dysfunction of a disease resulting from cerebral infarction, comprising:
    intravenously administering an effective amount of paraoxonase in combination with an effective amount of 3-[(3-cholamidopropyl)dimethylammonio]-1-propanesulfonate to improve one of prognosis, neurological symptoms and motor dysfunction of a disease resulting from cerebral infarction to a patient in need thereof,
    wherein the paraoxonase is a purified paraoxonase having a specific activity of not less than 500 $U/A_{280}$.

2. The method of claim 1, wherein the intravenously administering of the effective amount of paraoxonase comprises intravenously administering the effective amount of paraoxonase in the presence of a polyol.

3. The method of claim 1, wherein the intravenously administering of the effective amount of paraoxonase comprises intravenously administering the effective amount of paraoxonase in the presence of a glycerol.

4. The method of claim 1, wherein the paraoxonase is a purified paraoxonase having a specific activity in a range of 500 to 2000 $U/A_{280}$.

5. The method of claim 1, wherein the paraoxonase is a purified paraoxonase having a specific activity in a range of 500 to 1800 $U/A_{280}$.

6. The method of claim 1, wherein the intravenously administering of the effective amount of paraoxonase comprises intravenously administering an effective amount of a detergent to stabilize an activity of the paraoxonase in combination.

7. The method of claim 1, wherein the intravenously administering of the effective amount of paraoxonase comprises intravenously administering 3-[(3-cholamidopropyl)dimethylammonio]-1-propanesulfonate in an amount of about 0.01 w/v % to about 1 w/v % in combination with paraoxonase.

8. The method of claim 1, wherein the intravenously administering of the effective amount of paraoxonase comprises intravenously administering 3-[(3-cholamidopropyl)dimethylammonio]-1-propanesulfonate in an amount of 0.05 w/v % to 0.5 w/v % in combination with paraoxonase.

9. The method of claim 1, wherein the intravenously administering of the effective amount of paraoxonase comprises intravenously administering 3-[(3-cholamidopropyl)dimethylammonio]-1-propanesulfonate in an amount of 0.05 w/v % in combination with paraoxonase.

10. The method of claim 9, wherein paraoxonase is administered at a concentration of 10 mg/mL.

11. A method for improving prognosis, neurological symptoms, or motor dysfunction of a disease resulting from cerebral infarction, comprising:
    intravenously administering an effective amount of paraoxonase in combination with 3-[(3-cholamidopropyl)dimethylammonio]-1-propanesulfonate in an amount of about 0.01 w/v % to 1 w/v % once daily for 1 to 14 days to improve one of prognosis, neurological symptoms and motor dysfunction of a disease resulting from cerebral infarction to a patient in need thereof,
    wherein the intravenously administering of the combination is started within 48 hours after onset of a disease resulting from cerebral infarction, and the paraoxonase is a purified paraoxonase having a specific activity of not less than 500 $U/A_{280}$.

12. The method of claim 11, wherein the combination is administered intravenously once daily for 1 to 7 days.

13. The method of claim 12, wherein the combination is administered intravenously within 24 hours after onset of a disease resulting from cerebral infarction.

14. The method of claim 12, wherein the combination is administered intravenously within 12 hours after onset of a disease resulting from cerebral infarction.

15. The method of claim 12, wherein the combination is administered intravenously within 3 hours after onset of a disease resulting from cerebral infarction.

16. The method of claim 11, wherein the intravenously administering of the effective amount of paraoxonase comprises intravenously administering 3[(3-cholamidopropyl)dimethylammonio]-1-propanesulfonate in an amount of 0.05 w/v % to 0.5 w/v % in combination with paraoxonase.

17. The method of claim 11, wherein the intravenously administering of the effective amount of paraoxonase comprises intravenously administering 3-[(3-cholamidopropyl)dimethylammonio]-1-propanesulfonate in an amount of 0.05 w/v % in combination with paraoxonase.

18. The method of claim 17, wherein paraoxonase is administered at a concentration of 10 mg/mL.

* * * * *